United States Patent [19]
Spencer et al.

[11] Patent Number: 6,060,019
[45] Date of Patent: *May 9, 2000

[54] PLASMA-ENHANCED VACUUM DRYING

[75] Inventors: Robert M. Spencer, San Juan Capistrano; Tralance O. Addy, Cota de Caza, both of Calif.

[73] Assignee: Ethicon, Inc., New Brunswick, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/838,759

[22] Filed: Apr. 9, 1997

Related U.S. Application Data

[63] Continuation of application No. 08/320,932, Oct. 11, 1994, Pat. No. 5,656,238.

[51] Int. Cl.$^7$ .................................. A61L 2/14; A61L 2/20
[52] U.S. Cl. .................................. 422/23; 422/33; 34/257
[58] Field of Search .................................. 422/23, 28, 33, 422/186.05, 186.23, 186.25, 186.29, 906, 907; 34/92, 410, 415, 257; 250/455.11; 219/121.36, 385

[56] References Cited

U.S. PATENT DOCUMENTS

| | | | |
|---|---|---|---|
| 2,585,825 | 2/1952 | Nyrop | 34/257 |
| 2,972,196 | 2/1961 | Early et al. | . |
| 4,348,357 | 9/1982 | Bithell | 422/23 X |
| 4,507,539 | 3/1985 | Sando et al. | 8/444 X |
| 4,643,876 | 2/1987 | Jacobs et al. | 422/23 |
| 4,756,882 | 7/1988 | Jacobs et al. | 422/23 |
| 5,084,239 | 1/1992 | Moulton et al. | 422/23 X |
| 5,656,238 | 8/1997 | Spencer et al. | 422/23 |
| 5,667,753 | 9/1997 | Jacobs et al. | 422/29 |

FOREIGN PATENT DOCUMENTS 0 302 420 B1   2/1989   European Pat. Off. .

OTHER PUBLICATIONS

Sterilization Science, Chorine Dioxide as a Gaseous Sterilant, Joseph E. Knapp, David H. Rosenblatt and Aaron A. Rosenblatt, Sep. 1986.

American Society for Microbiology, Sporicidal Effect of Peracetic Acid Vapor, Dorothy M. Portner and Robert K. Hoffman, vol. 16, 1968, pp. 146–149.

Applied and Environmental Microbiology, American Society for Microbiology, Surface–Decontaminating Action of Glutaraldehyde in the Gas–Aerosol Phase, Ake Bovallius and Per Anas, Aug. 1977, pp. 129–134.

Ann. Rev. Microbiol. 15, Gaseous Sterilization, Carl W. Bruch, 1961, pp. 83–100.

Centr Steril, Overview of the Ethyene Oxide Alternative Sterilization Technologies, D.W. Janssen and P.M. Schneider, vol. 1, 1993, pp. 17–31.

*Primary Examiner*—Elizabeth McKane
*Attorney, Agent, or Firm*—Knobbe, Martens, Olson & Bear, LLP

[57] ABSTRACT

A plasma-enhanced vacuum drying method is disclosed. It is advantageously applied in plasma sterilization processes in particular, and represents a significant improvement for general evacuation drying methods. Articles to be sterilized are placed in a sealed chamber and the chamber is evacuated. A plasma of residual gas species is generated in the chamber during an initial evacuation step. This promotes drying of the articles and advantageously allows a desired pressure to be attained more quickly than without the plasma. Sterilizing gas is injected into the chamber, and a second plasma is generated to activate the sterilizing gas plasma, thereby sterilizing the articles in the chamber.

10 Claims, 8 Drawing Sheets

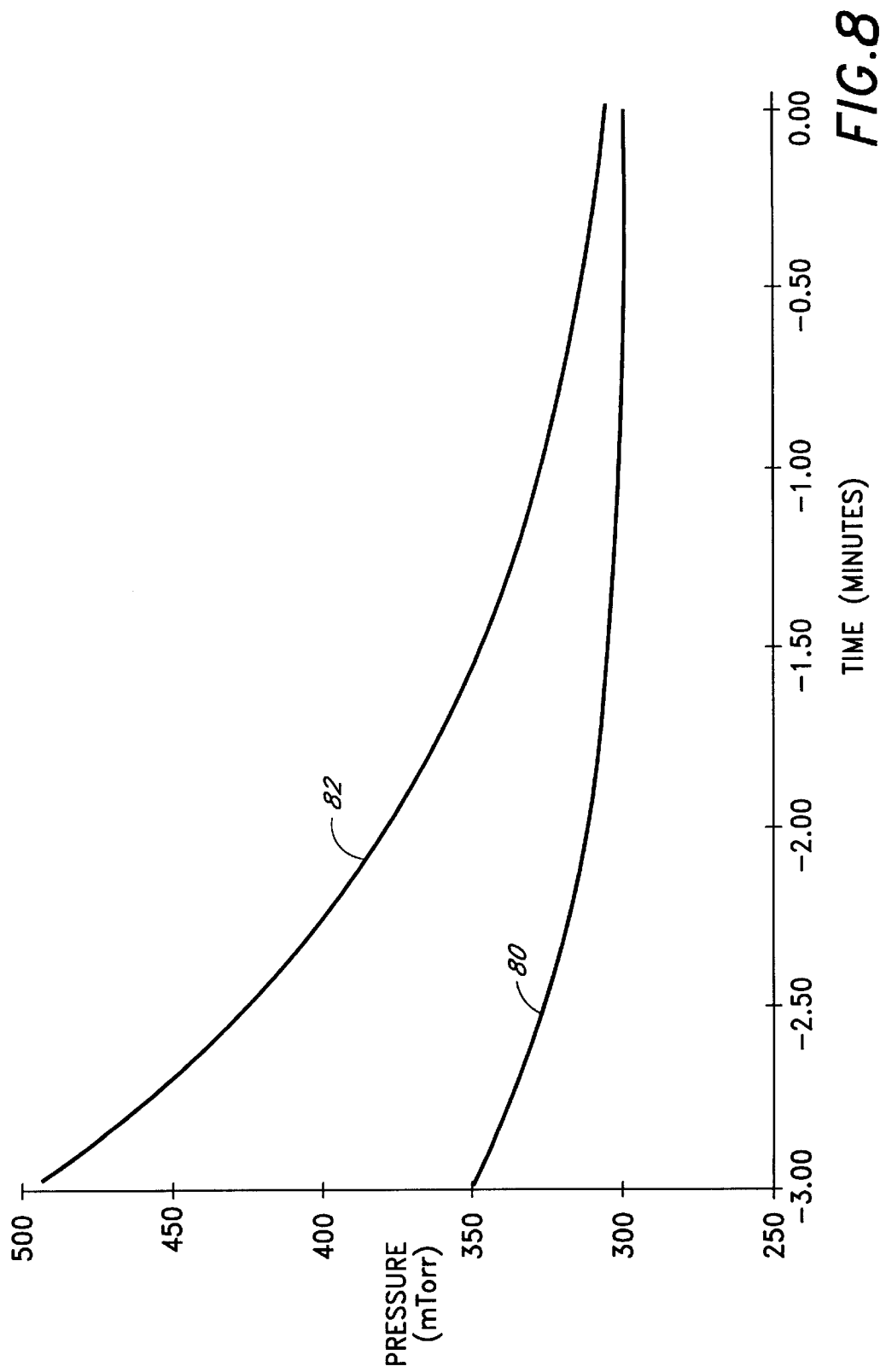

PLASMA-ENHANCED VACUUM DRYING

This application is a con of Ser. No. 08/320,932 filed Oct. 11, 1994 now U.S. Pat. No. 5,656,238.

FIELD OF THE INVENTION

The invention relates generally to methods of drying by evacuation. In particular, the invention pertains to enhanced vacuum drying using plasma excitation.

BACKGROUND OF THE INVENTION

Some new commercial systems for sterilizing medical instruments and the like utilize low-temperature reactive gas plasma to achieve rapid, low-temperature, low-moisture sterilization of medical items. Low-temperature gas plasma is sometimes described as a reactive cloud which may contain ions, electrons, and/or neutral atomic particles. This state of matter can be produced through the action of electric or magnetic fields, or through other external forces such as high-energy particle flux. In general, an electric field can be in any frequency range (An example of a naturally occurring plasma is the aurora borealis or the northern lights). One commercial embodiment of plasma sterilization is the STERRAD® Sterilization Process practiced by the assignee of the present application. The STERRAD® process is performed in the following manner. The items to be sterilized are placed in the sterilization chamber, the chamber is closed, and a vacuum is drawn. An aqueous solution of hydrogen peroxide is injected and vaporized into the chamber so that it surrounds the items to be sterilized. After reduction of the pressure in the sterilization chamber, a low-temperature gas plasma is initiated by applying radio frequency energy to create an electrical field. In the plasma, the hydrogen peroxide vapor is dissociated into reactive species that collide/react with and kill microorganisms. After the activated components react with the organisms or with each other, they lose their high energy and recombine to form oxygen, water, and other nontoxic byproducts. The plasma is maintained for a sufficient time to achieve sterilization and remove residuals. At the completion of the process, the RF energy is turned off, the vacuum is released, and the chamber is returned to atmospheric pressure by the introduction of High Efficiency Particulate-filtered Air (HEPA).

The above-described sterilization system can safely process medical items currently sterilized by ethylene oxide and steam, with the exception of linens, other cellulosic materials, powders, and liquids. Sterilized items are ready to be used in a little over an hour after starting the sterilizer. The process requires no aeration, and there are no toxic residues or emissions. Preparation of instruments for sterilization is similar to current practices: cleaning the instruments, reassembly, and wrapping. The system typically uses non-woven polypropylene wraps, which are commercially available, and a special tray and container system. A special adaptor placed on long, narrow lumen instruments allows rapid sterilization of their channels. A chemical indicator specifically formulated for this process is used, as well as a specifically designed biological indicator test pack.

The efficacy of the STERRAD plasma sterilization system has been demonstrated by: (1) killing a broad spectrum of microorganisms; (2) killing highly resistant bacterial spores in less than one-half of the full sterilization exposure cycle; (3) killing highly resistant bacterial spores on 16 different substrates commonly used in medical items. Depending upon the particular design plasma sterilization systems can therefore provide efficient, safe methods for sterilizing medical instruments and other hospital products.

For optimum operation, a plasma sterilization system such as that described above requires the loads that are to be sterilized to be quite dry. However, normal hospital practice in the preparation of instruments for sterilization often results in levels of water that may be excessive. The excess water makes it difficult to achieve the low-pressure thresholds required to initiate the sterilization process. To initiate the sterilization process, the chamber pressure is preferably reduced to relatively low levels, for example approximately 200–700 mTorr. Since the equilibrium vapor pressure of water is significantly higher than 700 mTorr at room temperature, any water in the chamber or load will begin to vaporize during the vacuum phase. The heat of vaporization required for the water to vaporize causes the load and any remaining water to chill. When enough water has vaporized, the remaining liquid begins to freeze. Eventually, the remaining liquid will completely freeze, which slows the rate of vapor generation and retards the attainment of the pressure levels required for optimum operation of the sterilizer. These conditions can cause undesirably long sterilization cycles or even cancellation of the sterilization cycle. To avoid this problem, a method is needed for preventing or removing any solid water in the vacuum chamber so that the desired pressure may be quickly achieved for sterilization.

Gaseous ion bombardment of surfaces in vacuo, commonly known as sputtering, is often used to remove adsorbed molecular species from surfaces and even to remove surface layers of the material itself. Although, it is known that noble gas plasma sputtering may enhance outgassing in high and ultra high vacuum systems, the energy and momentum exchange mechanisms between the plasma and surface can also lead to material damage of the surface as well as emission of the adsorbed species. Clearly, sputtering with the attendant material damage is unacceptable for a sterilization process.

SUMMARY OF THE INVENTION

According to the present invention, a method is provided for sterilizing an object in which the item to be sterilized is first placed in a sealed chamber. A vacuum is then applied to the chamber. At a first predetermined vacuum pressure, a plasma is generated in the chamber. This first plasma enhances the drying of the item to be sterilized by transferring energy to any ice or water which may be present inside the sterilizer, thereby promoting vaporization with evacuation. Preferably, the plasma generated at the first pressure is terminated after a period of time which is proportional to the quantity of wetting agent present. The vacuum is further applied to reach a second predetermined vacuum pressure which is lower than the first pressure. Finally, a sterilizing gas is injected into the chamber and radio frequency or other energy may be applied to generate a plasma with the sterilizing gas. After a sufficient time has elapsed for the item to be completely sterilized, the chamber is vented to atmospheric pressure and the article is removed.

According to another aspect of the present invention, the first predetermined vacuum pressure is approximately 700 mTorr, and the second predetermined level is approximately 300 mTorr. While the plasma is being generated, the vacuum continues to be drawn until a pressure of approximately 300 mTorr has been reached. Alternatively, the RF generator may be engaged for a predetermined period of time, after which the RF generator is switched off while continuing to evacuate the chamber. When the second predetermined level has been reached, a reactive fluid such as hydrogen peroxide is introduced into the sterilizer. The fluid is allowed to diffuse throughout the sterilizer for a number of minutes and then a second vacuum is drawn inside the sterilizer. When a vacuum of approximately 500 mTorr has been reached, the RF generator is then energized for a second time. In the plasma sterilization apparatus, the RF energy initiates a plasma of the remaining air molecules and molecules of the sterilizing gas transforming them into a number of highly reactive species. These reactive species attack any micro organism present in the chamber, inactivating them. After the RF generator has been engaged for a sufficient time and the sterilization process is complete, the RF generator is turned off and the vacuum is vented to atmospheric pressure through a suitable filter.

By aiding in the removal of water from the sterilizer, the plasma drying technique of the present invention advantageously reduces the time required to draw the required vacuum inside the sterilizer during the initial phase of the sterilization process. Indeed, if large amounts of water are present in the material to be sterilized, it may not be possible to draw the required vacuum within a reasonable time without using the plasma vacuum drying technique of the present invention. Consequently, the sterilization operation can be conducted in a much shorter time than otherwise possible by use of the method of the present invention.

The plasma enhanced drying process is of course useful in itself as a low-temperature evacuation dryer independent of the sterilization process. In accordance with another aspect of the present invention, ambient air in the volume surrounding a quantity of condensed material is evacuated to promote vaporization. Preferably the volume is evacuated to a pressure substantially at or less than the equilibrium vapor pressure of the condensed material. Such a condensed material may for example be water or ice but may also be other volatile wetting agents. A residual gas plasma is excited in the evacuated volume to advantageously promote vaporization during evacuation or intermittently with evacuation. The method of plasma enhanced drying according to the present invention is particularly suited for removing quantities of water that would otherwise freeze to form ice, substantially slowing conventional evacuation drying methods.

BRIEF DESCRIPTION OF THE FIGURES

FIG. 6 shows vacuum profiles of pump-down performance.

FIG. 8 is a plot of evacuation performance for vacuum drying with and without plasma enhancement.

DETAILED DESCRIPTION OF THE PREFERRED EMBODIMENTS

Figure 1:
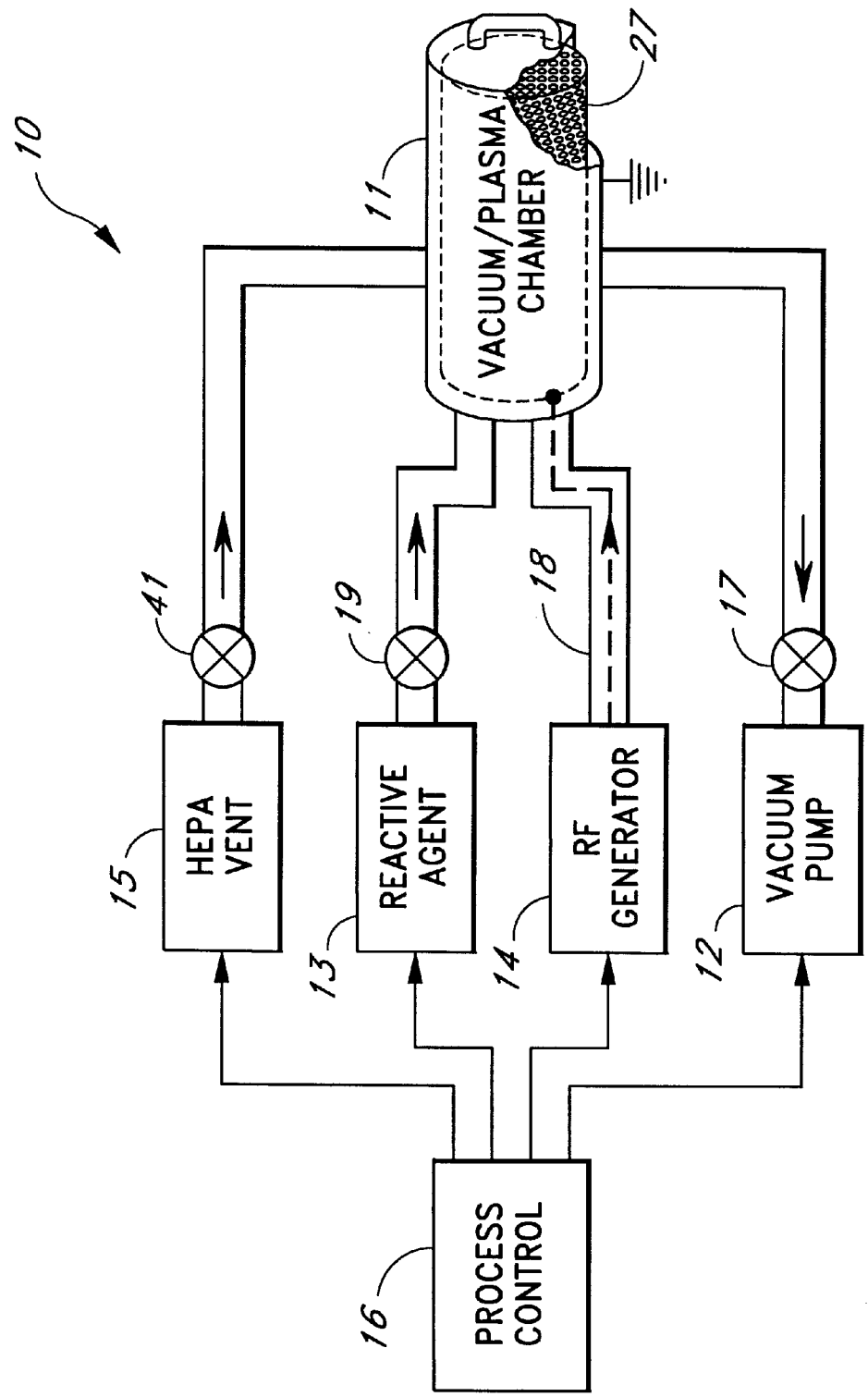
FIG. 1 is a simplified diagram of a plasma sterilization apparatus.

Referring to the drawings, FIG. 1 depicts a plasma sterilizer in block diagram form generally at 10. The sterilizer 10 and its components and methods of use are described more fully in U.S. Pat. No. 4,756,882, issued Jul. 12, 1988 and assigned to the assignee of the present application. This patent is incorporated by reference herein. The sterilizer includes a vacuum and plasma chamber 11; a vacuum pump 12 connected to the electrode 11 by a valve 17; and a source of suitable reactive agent 13 such as hydrogen peroxide and connected to the vacuum chamber 11 by a line having a valve 19 therein. The sterilizer 10 also includes an RF generator 14 electrically connected to the plasma generator inside the vacuum chamber 11 by a suitable coupling 18, as well as a HEPA vent 15 connected to the vacuum chamber via a line and a valve 41. A process control logic 16, preferably a programmable computer, is connected to each of the components which are connected to the vacuum chamber 11. The process control logic 16 directs the operation of each of the components connected to the vacuum chamber at the appropriate time to effectuate the sterilization operation.

The vacuum chamber 11 contains the objects to be sterilized and is sufficiently gas-tight to support a vacuum of less than 300 mTorr. Inside the chamber 11 is an RF antenna, or electrode array 27 to which the RF energy is supplied. In a preferred embodiment the electrode is arranged such that it is tubuler and equidistant from the chamber 11 wall to produce a symmetric RF electric field distribution. The electrode excites a plasma when an RF potential is applied by the RF generator 14 through the RF coupling 18. The RF coupling 18 may be a coaxial cable or other such waveguide capable of transmitting high power RF energy without significant impedance loss connected to an impedance matching device for the electrode.

The vacuum pump 12 and connecting valve 17 comprise a conventional arrangement well known in the art. The vacuum pump is typically a mechanical vacuum pump such as the rotary vane variety, capable of drawing a vacuum in the dry vacuum chamber 11 of approximately 300 mTorr or less within approximately 5 minutes of pumping. The valves 17 should have sufficient integrity to seal a vacuum of less than 300 mTorr without significant leakage. This requirement also applies to the other valves 19 and 41 present in the sterilizer.

The RF generator 14 is a conventional RF oscillator well known in the art, such as for example a solid-state or a vacuum tube oscillator with RF power amplification. The combination may generate RF energy in a frequency range of 0.1 MHz to 30 MHz and powers ranging from 50 W to 1500 W, and preferably a frequency of 13.56 MHz and power greater than 100 W.

Figure 2:
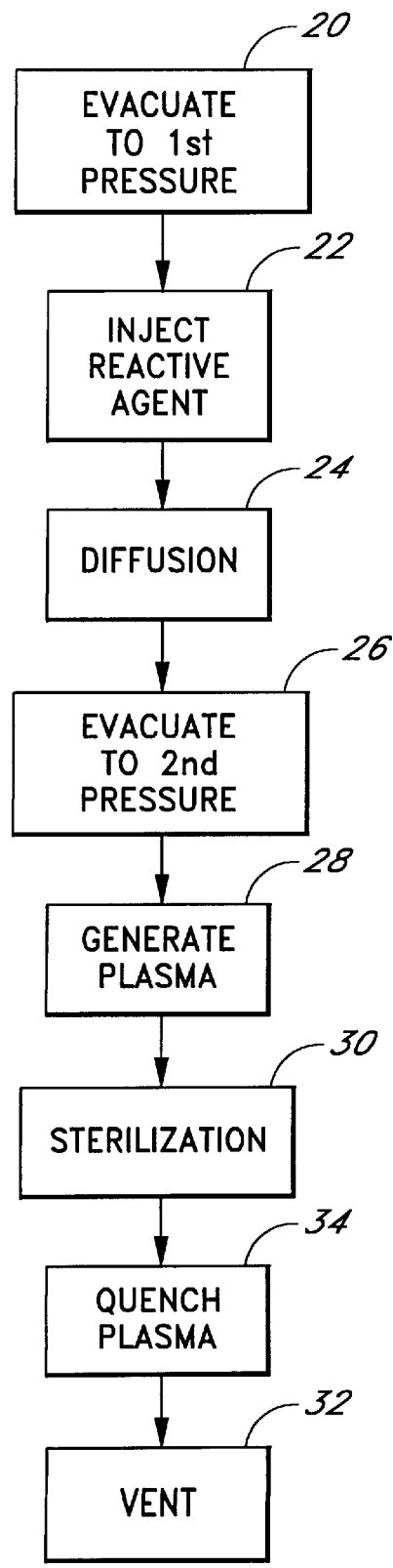
FIG. 2 is a block diagram of a plasma sterilization process.
Figure 3:
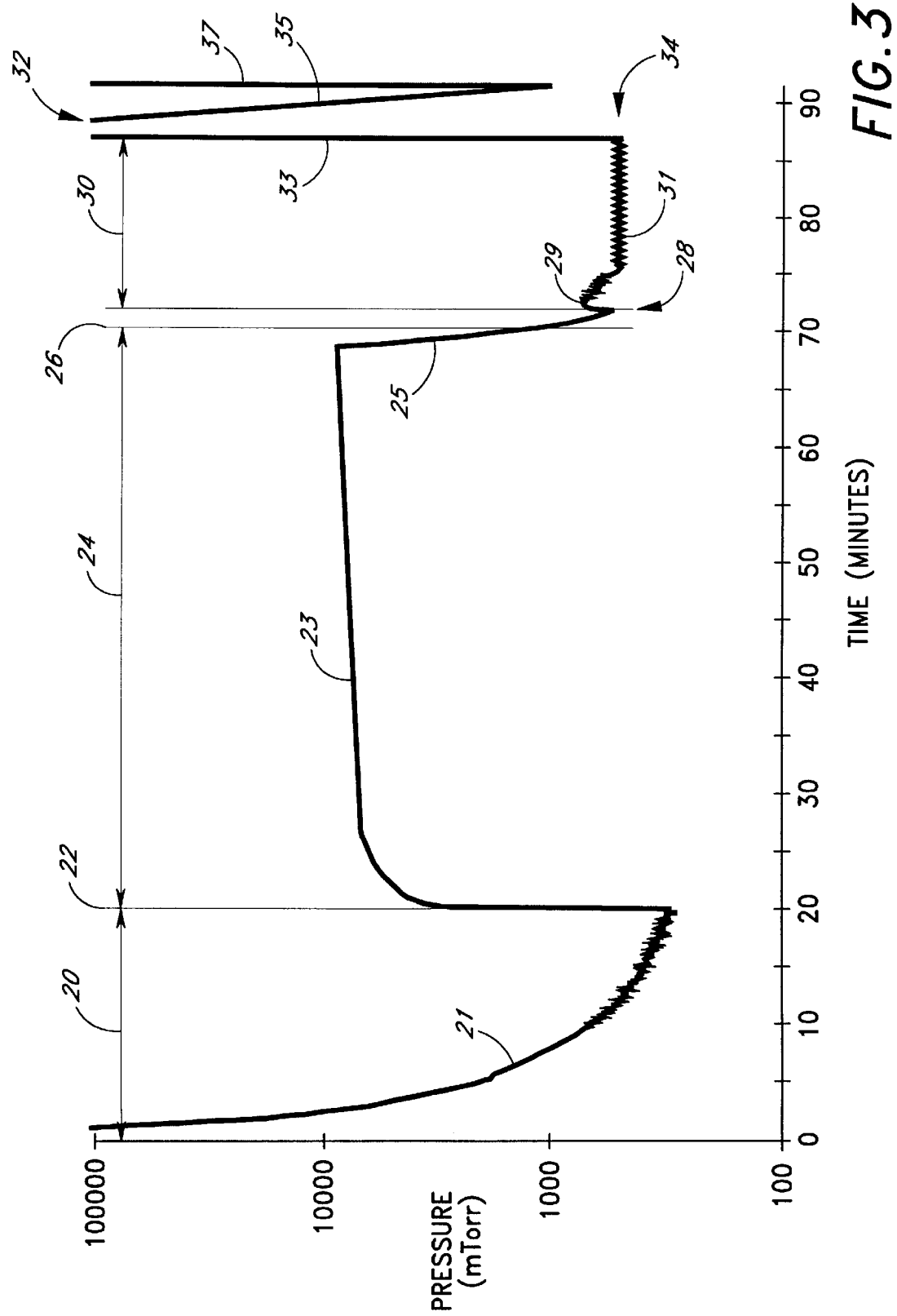
FIG. 3 is a vacuum profile of a plasma sterilization process.

Operation of the plasma sterilizer 10 without the plasma-enhanced drying technique of the present invention is described in schematic form in FIGS. 2 and 3, which respectively illustrate the sequence of operations employed by the sterilizer 10 and the corresponding pressure in chamber 11 as a function of time.

After the objects to be sterilized have been placed in the vacuum chamber and the chamber has been sealed, the process control logic 16 engages the vacuum pump 12 and valve 17 to evacuate the chamber to a pressure substantially at or below the equilibrium vapor pressure of the wetting agent, in this case water, as indicated by step 20. The pressure inside the vacuum chamber is tracked by the curve 21 in FIG. 3. The pressure drop generally follows a non-linear path, often accurately described by first-order differential behavior. Under such circumstances, water or other such condensed solvent can act as a reservoir for residual vapor, limiting evacuation rate and possibly even base-pressure. Hence, the time required to attain a desired pressure is strongly dependent on the amount of water present on the objects to be sterilized, as indicated by the evacuation performance curves of FIG. 4. Curve 52 shows the evacuation time for an empty chamber 11, while curves 58, 60 and 62 shows the evacuation performance for water bearing loads of 500 μl, 600 μl and 2500 μl respectively. In the present exemplary sterilization process, it is preferable to attain a chamber pressure of 300 mTorr within a 20 minute evacuation time span. Clearly the evacuation and drying time can become unacceptably long for even typical quantities of residual water, as would be encountered in hospital cleaning processes.

The process of vacuum vaporization causes heat transfer between the load, including the condensed water, and the portion of water undergoing vaporization (i.e. heat of vaporization). Since the load and condensed water are thermally isolated (e.g. in a vacuum) they cool as vaporization occurs during evacuation step 20. Cooling can cause the remaining water to transition the triple point and freeze, thus further slowing the evacuation step 20. This frozen water may be removed from the chamber only by the much slower process of sublimation, which significantly increases the time required to dry the load and evacuate the chamber to the required pressure. Consequently, a considerable length of time may be required to evacuate chamber 11 during the initial step 20.

When a desired vacuum threshold has been reached, the reactive sterilization agent 13 is injected during step 22. The injection of the sterilization agent during step 22 causes the pressure inside the vacuum chamber to rapidly rise; in the preferred embodiment, the pressure may rise to a level of approximately 5000 mTorr or more, as indicated by the curve 23 in FIG. 3. The injection phase may take approximately 6 minutes. After the sterilization agent is injected into the chamber, it is allowed to diffuse completely and evenly throughout the vacuum chamber during step 24. This step typically lasts approximately 45 minutes, at which time the sterilization agent should be substantially in equilibrium inside the vacuum chamber 11.

At the end of the diffusion period, the process control logic 16 again engages the vacuum pump 12 and opens the valve 17 to pump down the chamber 11 to a vacuum of approximately 500 mTorr during step 26. The pressure inside the vacuum chamber rapidly drops to a value of 500 mTorr, as indicated by the curve 25 in FIG. 3. When the pressure inside the chamber 11 has reached 500 mTorr, the process control logic 16 commands the RF generator 14 to generate an RF signal which is transmitted to the plasma generator. This action causes a gas plasma to be created inside the vacuum chamber during step 28. The components of the plasma are dissociation species of the reactive agent as well as molecules of residual gas remaining in the chamber 11.

Generating the plasma induces a brief rise in pressure, as indicated by the pressure immediately after step 28. The plasma generator remains energized for approximately 15 minutes during the sterilization step 30, and the plasma it creates can effectively destroy any pathogens present in the vacuum chamber 11. The sterilization process is conducted at an approximately constant pressure of 500 mTorr, as indicated by curve 31 in FIG. 3.

After the sterilization process is complete, the chamber 11 is vented through the HEPA vent 15 during the venting step 32. This venting step is indicated by the curve 33 in FIG. 3.

A final vacuum application is undertaken to flush any remaining sterilizing agent which may be present in the chamber. A vacuum of approximately 1 Torr is quickly drawn, as indicated by curve 35 in FIG. 3. Following this step, the vacuum chamber is again vented to atmospheric pressure through the HEPA vent 15, as indicated by the curve 37, and the sterilized articles are removed from the chamber.

Figure 5:
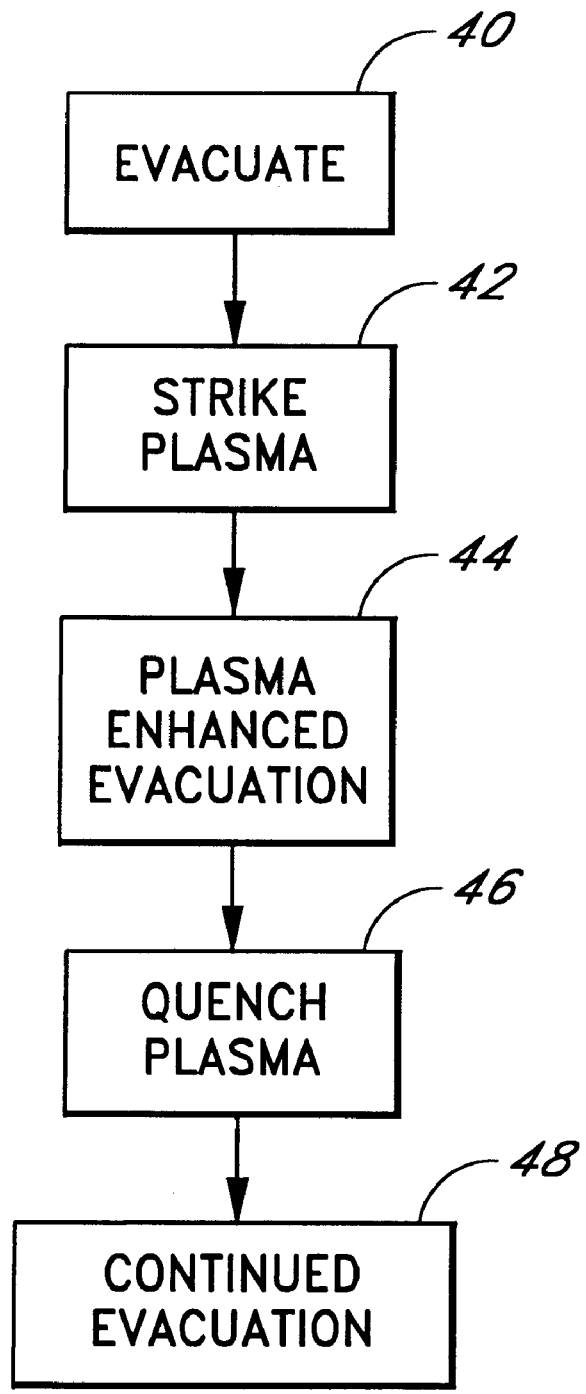
FIG. 5 is a block diagram of a plasma-enhanced vacuum drying process.
Figure 6:
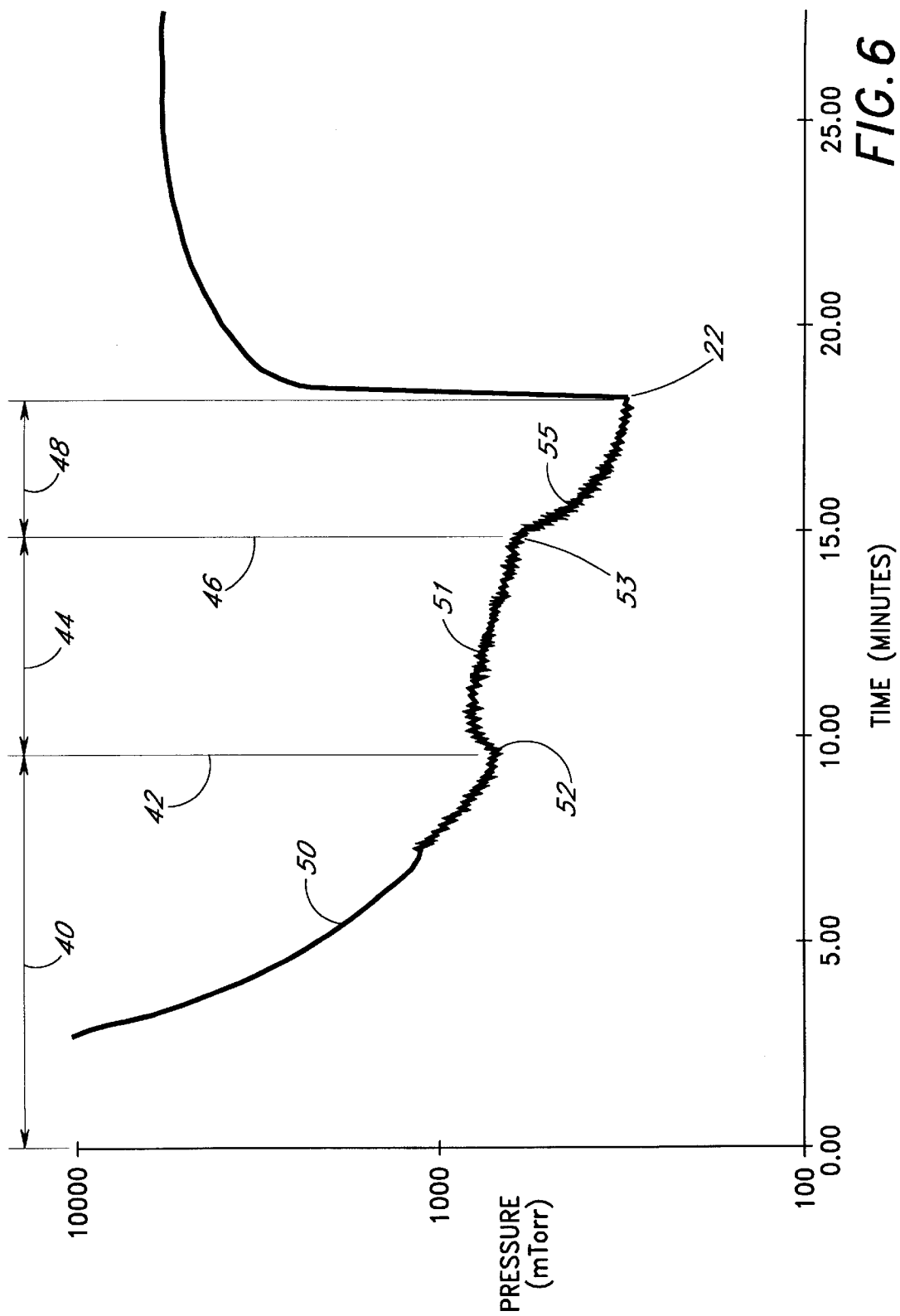
FIG. 6 is a vacuum profile of a plasma-enhanced drying process.

A preferred method of plasma-enhanced drying according to the present invention is disclosed in the context of the aforementioned sterilization method, and described with respect to FIGS. 5 and 6. It is understood that in all other respects, the operation of the sterilizer 10 described above is the same. It is also understood that the plasma enhanced drying can be applied to a wide variety of vacuum applications in addition to the plasma sterilization described.

After the articles to be sterilized are introduced into the chamber 11 and the chamber 11 is sealed, the vacuum pump 12 and valve 17 are energized to evacuate the chamber 11 to a predetermined pressure, in this case a pressure of about 700 mTorr, as indicated by step 40 in FIG. 5. The chamber pressure generally behaves as shown by curve 50 of FIG. 6. When the desired pressure has been reached, the process control logic 16 transmits a command to the RF generator 14 to energize the electrode within the chamber 11, as indicated by step 42. This action causes a gas plasma to be created inside the chamber 11 comprised of residual gas species. It will be appreciated that other chamber and electrode configurations as well as RF generators may render appreciable variation in the pressure range over which a plasma may be supported. Moreover, various other conditions such as solvent content, process time, temperature and equilibrium vapor pressure will determine the conditions under which plasma enhancement is most desirable. In the present embodiments herein disclosed the plasma tranfers energy to the condensed water thereby aiding the vaporization process. While such energy transfer serves to increase the water temperature, it is preferred that the plasma does not chemically or physically alter the load surfaces as is commonly encountered in a sputtering or plasma chemical process. Thus, the plasma should preferably have average energy and momentum characteristics sufficient to impart heat energy to the condensed water, while leaving the load surface molecules and molecular bonds intact. In the present embodiment, the plasma is usually generated when the chamber pressure is approximately 700 mTorr, whereas at higher pressures such generation may be limited due to the impedance between the chamber 11 and the RF generator 14. Furthermore, plasma generation at about 700 mTorr substantially minimizes the total process time required to reach a pre-sterilization pressure of 300 mTorr.

Figure 7:
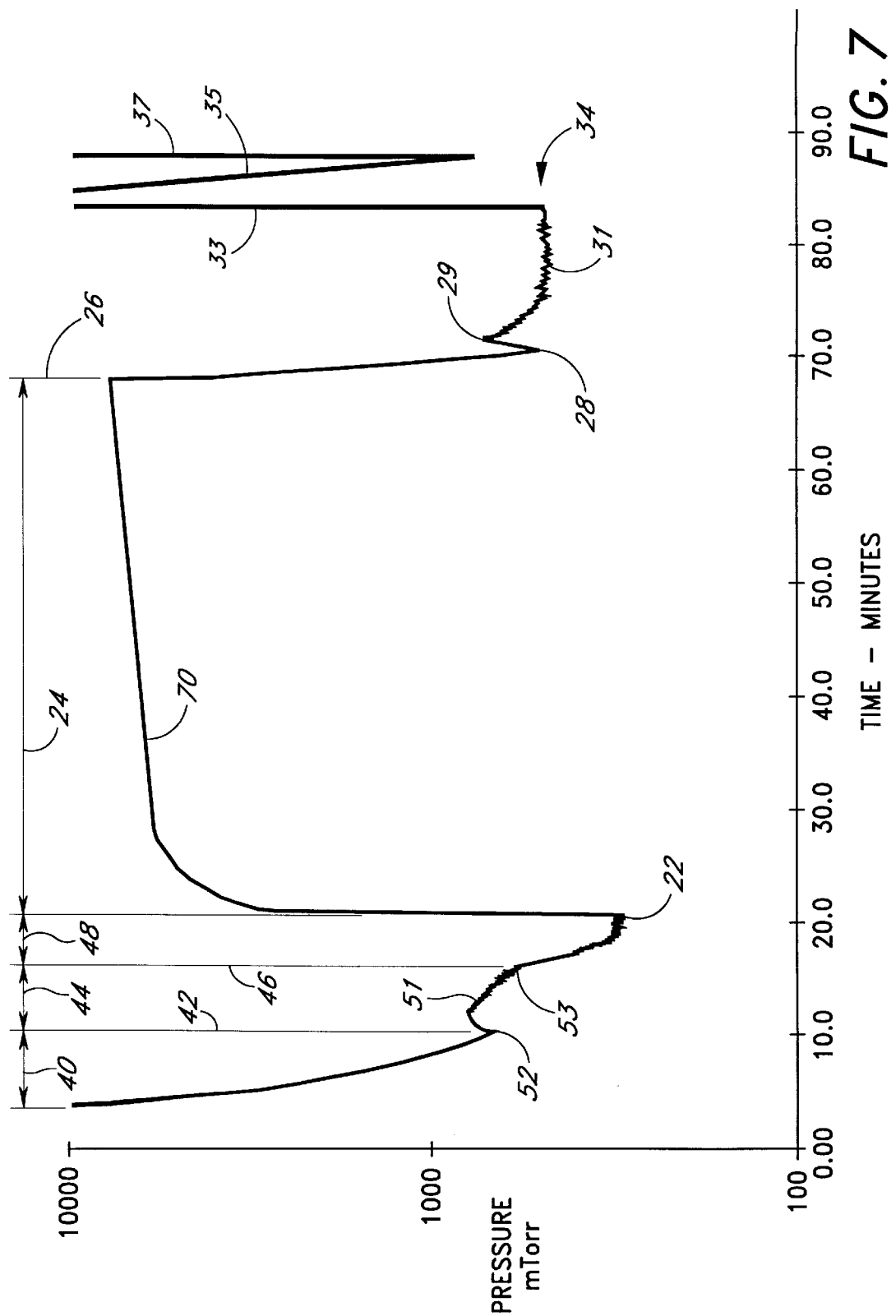
FIG. 7 is a vacuum profile of a plasma sterilization process using plasma-enhanced vacuum drying.

The creation of the residual gas plasma causes the pressure to rise inside the chamber, indicating enhanced vapor generation, as shown by the cusp 52 of curve section 51 in FIG. 6. While plasma is being generated, the vacuum pump 12 remains engaged to further evacuate the chamber concurrent with this period of enhanced vapor generation as indicated by step 44. After a period of time, in this case approximately 5–15 minutes of operation, the plasma generator is turned off, step 46, and the evacuation continues during step 48. In this exemplary embodiment, evacuation continues until a pressure of approximately 300 mTorr is attained. As indicated by a second cusp 53 in curve 51 of FIG. 5, evacuation proceeds at a higher rate upon quenching the residual gas plasma, indicating a reduced rate of vaporization. In the present preferred embodiment the period over which the plasma enhanced evacuation 44 operates is determined by a maximum desirable evacuation time of 20 minutes to reach a desired pressure of 300 mTorr. It will be appreciated that there are many variations in the manner in which the plasma-enhanced evacuation 44 is implemented in a drying or sterilization process. In the present exemplary embodiment, the plasma enhanced evacuation 44 is initiated at a predetermined pressure and may be terminated after a period of time or upon reaching a second predetermined pressure. A vacuum profile of an entire sterilization process utilizing plasma-enhanced drying is shown in FIG. 7, where process step 20 is replaced by process steps 40–48. After the evacuation and drying process steps 40–48, the remainder of the sterilization process is substantially similar to the aforementioned sterilization process steps. As indicated in FIG. 7, plasma-enhanced drying is conveniently incorporated into the initial evacuation phase, requiring no additional material or construction.

Figure 4:
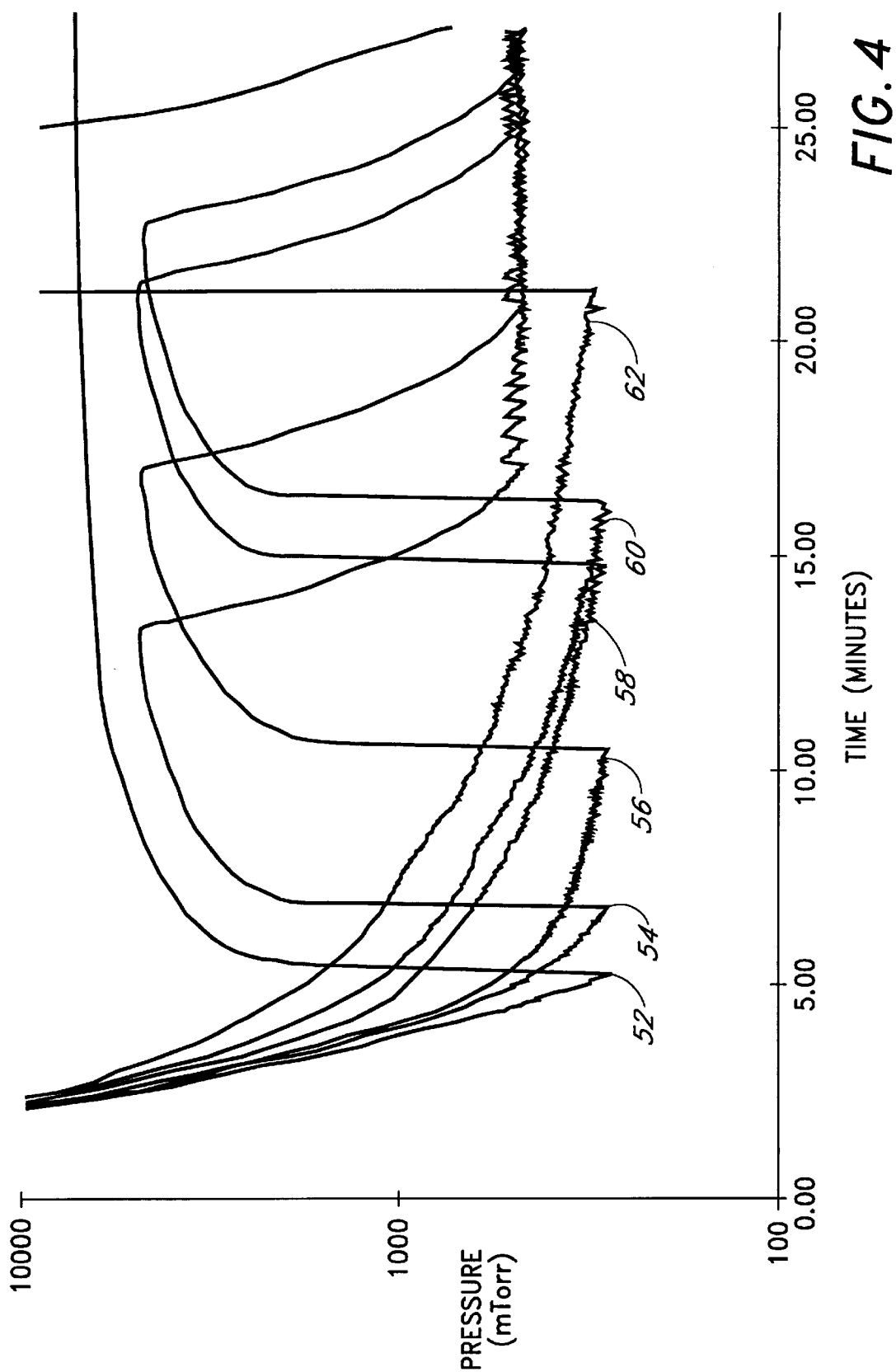
FIG. 4 is a plot of evacuation characteristics for various process loads.

As shown in FIG. 4, the plasma-enhanced drying technique of the present invention substantially decreases the time required for the vacuum pump 12 to reduce the chamber pressure required for the operation of the sterilizer 10. Performance curves 54 and 56 represent the chamber pressure as a function of time during evacuation for representative loads with and without a plasma-enhanced vacuum drying process respectively. FIG. 8 is a plot of evacuation performance for evacuation after plasma-enhancement 82 and without plasma enhancement 80 as the chamber pressure approaches a nominal final pressure of about 300 mTorr. Indeed, as shown in FIG. 8, the evacuation rate after plasma excitation, curve 82, is considerably higher than by vacuum evacuation alone, curve 80. A comparison of these data indicates that the performance gain realized through use of plasma-enhanced drying is substantial. The present invention achieves this result because the plasma generated during step 42 transfers energy from the RF generator to the liquid present in the chamber. The energy transferred to the liquid promotes vaporization and hence speeds the drying process.

This gain in performance represents an increase in the effective pump efficiency during the initial evacuation/drying stages 40–48, and results in faster, more consistent operation of the sterilizer 10. It has been found that plasma-enhanced drying is most useful when the time taken by the vacuum pump 12 to reach a pressure of 1 Torr during stage 40 is between 5 and 9 minutes. If this time is less than 5 minutes, the items in the chamber are already reasonably dry and plasma-enhanced drying may not greatly speed up the drying process. If, on the other hand, this time is greater than 9 minutes, the items in the chamber may be too wet to process by the sterilizer as presently constituted. The values disclosed herein are valid for the particular configuration of the current embodiment. However, these values may differ substantially to maximize the benefit of the invention for other configurations. It has been determined in practice that application of the plasma for a duration of time proportional to the wetness of the objects in the chamber results in optimum drying of the materials placed therein. However, durations longer than 15 minutes have been found to decrease the chance of reaching the desired pre-sterilization pressure of 300 mTorr inside the chamber 11 within the desired 20 minute duration (the maximum time presently allowed in a commercial embodiment of the sterilizer 10) of initiation of the vacuum pumping step 40.

An additional advantage of the present invention is that plasma enhanced drying may be applied to the full complement of load material types compatible with the plasma sterilizing process without perceptible physical or chemical damage. Finally, a residual gas or other such plasma intended for enhancing vaporization can be energetically tailored by varying gas species and applied RF power to render an efficient energy transfer to a variety of wetting agents. It is particularly advantageous for applications requiring low temperature vacuum drying, and furthermore is not limited to aqueous wetting agents.

While the present invention has been described with respect to use in a sterilization system, it should, of course, be understood that plasma-enhanced vacuum drying can be applied to other systems in which it is desirable to improve drying efficiency for objects in vacuum. In this regard the invention may be useful as simply a dryer if the load to be dried includes at least one milliliter of water.

What is claimed is:

1. A vacuum sterilization method, comprising:

placing into a chamber an article to be sterilized, said article having a quantity of condensed residue thereon to be evaporated, wherein said condensed residue comprises water;

evacuating the chamber to reach a pressure selected to facilitate evaporation of said residue, and leaving a residual gas in said chamber;

generating a gas plasma in the chamber at said pressure from said residual gas;

maintaining the gas plasma in the chamber for a duration sufficient to evaporate a substantial portion of the condensed residue; and introducing a sterilizing gas comprising hydrogen peroxide into the chamber subsequent to evaporation of the substantial portion of the condensed residue at a pressure selected to facilitate sterilization.

2. The method of claim 1, wherein the duration of plasma generation is proportional to the quantity of condensed residue to be evaporated.

3. The method of claim 1, wherein the vacuum pressure at which the plasma is generated is approximately 700 mTorr.

4. The method of claim 1, including exciting the plasma substantially at or below the equilibrium vapor pressure of the condensed residue.

5. The method of claim 1, wherein the gas plasma in the chamber is generated from said residual gas.

6. The method of claim 1, further comprising generating plasma after introducing said sterilizing gas comprising hydrogen peroxide.

7. The method of claim 1, further comprising venting said chamber.

8. The method of claim 1, wherein at least one step is repeated at least once.

9. The method of claim 1, wherein the entire method is repeated at least once.

10. The method of claim 1, wherein said gas plasma is generated at a pressure at or below the equilibrium vapor pressure of said condensed residue.

* * * * *